United States Patent
Dinney

(10) Patent No.: US 12,178,865 B2
(45) Date of Patent: Dec. 31, 2024

(54) CDKN2A COMPANION DIAGNOSTIC FOR BLADDER CANCER INTERFERON THERAPY

(71) Applicant: Trizell Limited, West Drayton (GB)

(72) Inventor: Colin P. Dinney, Houston, TX (US)

(73) Assignee: Trizell Limited, West Drayton (GB)

( * ) Notice: Subject to any disclaimer, the term of this patent is extended or adjusted under 35 U.S.C. 154(b) by 0 days.

(21) Appl. No.: 17/965,739

(22) Filed: Oct. 13, 2022

(65) Prior Publication Data

US 2023/0310566 A1    Oct. 5, 2023

Related U.S. Application Data

(62) Division of application No. 16/458,275, filed as application No. PCT/US2018/064829 on Dec. 11, 2018, now abandoned.

(60) Provisional application No. 62/597,473, filed on Dec. 12, 2017.

(51) Int. Cl.
| | |
|---|---|
| A61K 39/04 | (2006.01) |
| A61K 45/06 | (2006.01) |
| A61K 48/00 | (2006.01) |
| C07K 14/56 | (2006.01) |
| C12N 7/00 | (2006.01) |
| C12N 15/86 | (2006.01) |
| C12Q 1/6886 | (2018.01) |

(52) U.S. Cl.
CPC ............ *A61K 39/04* (2013.01); *A61K 45/06* (2013.01); *C07K 14/56* (2013.01); *C12N 7/00* (2013.01); *C12N 15/86* (2013.01); *C12Q 1/6886* (2013.01); *A61K 48/00* (2013.01); *C12N 2750/14143* (2013.01); *C12Q 2600/106* (2013.01); *G01N 2800/00* (2013.01); *G01N 2800/7028* (2013.01)

(58) Field of Classification Search
None
See application file for complete search history.

(56) References Cited

U.S. PATENT DOCUMENTS

| | | | | |
|---|---|---|---|---|
| 9,551,713 B2 * | 1/2017 | Kamat | ............. | G01N 33/57407 |
| 2013/0059303 A1 * | 3/2013 | Radvanyi | ............. | C12Q 1/6886 |
| | | | | 435/6.11 |

FOREIGN PATENT DOCUMENTS

| | | | | |
|---|---|---|---|---|
| WO | WO-2014036525 A1 * | 3/2014 | ........... | C12Q 1/6806 |
| WO | 2019118389 A1 | 6/2019 | | |

OTHER PUBLICATIONS

FKD Therapies (Study NCT02773849, Nov. 21, 2017) (Year: 2017).*
Exosomedx (Plasma-based solid tumor mutation panel, Dec. 23, 2016) (Year: 2016).*
Bellmunt, J. et al., A Review on the Evolution of PD-1/PD-L1 Immunotherapy for Bladder Cancer: The Future Is Now, Cancer Treatment Reviews, 54:58-67 (2017).
Exosome Diagnostics, Inc. Plasma-Based Solid Tumor Mutation Panel ExoDx Solid Tumor. Dec. 23, 2016, pp. 1-2; p. 1, first paragraph; p. 1, Solid Tumor Mutation Panel Performance; p. 1, Genes Covered in Our Solid Tumor Mutation Panel; p. 1, Key Benefits; p. 2, Benefits of Working With Exosome Diagnostics.
FKD Therapies Oy. Study NCT02773849: A Study to Evaluate INSTILADRIN in Patients with High-Grade, Bacillus Calmette-Guerin (BCG) Unresponsive NMIBC. Nov. 21, 2017 [online] [retrieved on Feb. 25, 2019]; Retrieved from the internet <URL: https://clinicaltrials.govict2/history/NCT02773849?A=16&B=16 &C=merged#StudyPageTop>, p. 3, Study Description; p. 4, Arms and Interventions.
International Search Report for PCT/US2018/064829, 3 pages (mailed Mar. 15, 2019).
Joudi, F. N. et al., Final results from a national multicenter phase II trial of combination bacillus Calmette-Guerin plus interferon ?-2B for reducing recurrence of superficial bladder cancer, Urology Oncology: Seminars and Original Investigations, 24(4):344-348 (2006).
Kojima, T. et al., Biomarkers for precision medicine in bladder cancer, International Journal of Clinical Oncology, 22(2):207-213 (2016).
Meeks, J. et al., Genomic characterization of high-risk non-muscle invasive bladder cancer, Oncotarget, 7(46):75176-75184 (2016).
Shore, N. et al., Intravesical rAd-IFNa/Syn3 for Patients with High-Grade, Bacillus Calmette-Guerin-Refractory or Relapsed Non-Muscle-Invasive Bladder Cancer: A Phase II Randomized Study, Journal of Clinical Oncology, 35(30):3410-3416 (2017).
Written Opinion for PCT/US2018/064829, 6 pages (mailed Mar. 15, 2019).
Yates, D. R. and Roupret, M., Contemporary management of patients with high-risk non-muscle-invasive bladder cancer who fail intravesical BCG therapyl 1, World Journal of Urology, 29(4):415-22 (2011).

* cited by examiner

*Primary Examiner* — Sergio Coffa
(74) *Attorney, Agent, or Firm* — Lisa Mueller; Casimir Jones SC

(57) ABSTRACT

A method of treating bladder cancer comprising diagnosing bladder cancer in a human, measuring the human's level of CDKN2A expression, and then instilling into the human an agent which induces interferon expression.

16 Claims, No Drawings

CDKN2A COMPANION DIAGNOSTIC FOR BLADDER CANCER INTERFERON THERAPY

RELATED APPLICATIONS

This application claims priority from United States provisional patent filing Ser. No. 62/597,473 filed 12 Dec. 2017, the contents of which are here incorporated by reference.

UNITED STATES GOVERNMENT FUNDING/INTEREST

None

BACKGROUND

Non-muscle-invasive bladder cancer (NMIBC) represents the most common disease state for patients with newly diagnosed bladder cancer Those with high-grade (HG) tumors are at significant risk for both recurrence and progression. *Bacillus* Calmette-Guerin (BCG) represents the current preferred management. Nonetheless, approximately 30% of patients will not respond to BCG; among those who demonstrate an initial response, more than 50% will experience recurrence and progression during long-term follow-up.

The optimal management of patients with persistent or recurrent tumor after BCG remains controversial. Although radical cystectomy provides cancer eradication, many patients are elderly, have significant co-morbidities with an attendant diminished performance status, and often are unwilling to undergo radical extirpative surgery. Nonextirpative treatment options are available, but studies to date have included relatively small patient numbers and used varied definitions of treatment success. Indeed, the US Food and Drug Administration (FDA) and genitourinary oncology community agree that scant progress has been made in the management of this disease since the initial approval of BCG. Thus an effective alternative to radical cystectomy for patients with disease recurrence after BCG treatment remains an important unmet clinical need.

Several agents have been evaluated as second-line treatment after BCG; however, none (to date) have provided robust and durable responses. Valrubicin (Valstar; Endo Pharmaceuticals, Malvern, PA), the only agent currently approved by the FDA for the treatment of BCG-refractory CIS, provided a complete response rate of 18% at 6 months and a 1-year disease-free survival rate of approximately 10%. Promising results from early-phase trials have been reported for intravesical taxane and gemcitabine. Joudi et al. reported the final results from a national multicenter phase II trial of BCG plus IFNα-2b and noted that 45% of patients with BCG failure were free from recurrence at 2 years. However, only 44% were treated for an HG recurrence, and 61% received only one prior course of BCG. A recent retrospective analysis of BCG and IFNα-2b reported a 38.6% RFS at 12 months. Again, many of these patients (20 of 44) received only one prior course of BCG, and 16 patients experienced relapse after 12 months. Overall, the limited number of patients studied in previous trials, as well as the modest RFS with treatment despite a less stringently defined eligibility, illustrates the unmet need for effective and evidence-based second-line therapy for patients with BCG-unresponsive disease that improves disease-specific patient outcomes and avoids cystectomy.

Recombinant intravesical interferon alfa-2b protein (IFNα-2b: Intron A, Merck, Kenilworth, NJ) demonstrated promising initial clinical results in NMIBC.

Intravesical IFNα-2b gene delivery offers a novel approach and increases the duration of exposure to IFNα-2b. Recombinant adenovirus (rAd)-IFNα-2b is a replication-deficient adenovirus-based gene transfer vector that encodes the human IFNα-2b gene. Syn3, a polyamide surfactant, is incorporated into the drug formulation (INSTILADRIN® rAd-IFNα/Syn3™, FKD Therapies Oy, Kuopio, Finland) to enhance adenoviral transduction of the bladder lining.

Dramatic enrichment of rAd-IFNα gene transfer and expression has been shown with Syn3™ in both normal urothelium and human urothelial carcinoma that grows in mice rAd-IFNα-2b gene therapy mimics the physiologic events associated with viral infection, which results in local rather than systemic IFNα-2b production and subsequent tumor regression.

We performed a phase I dose-ascending study of rAd-IFNα/Syn3 for patients with BCG-refractory and relapsing NMIBC. First-generation replication-deficient serotype 5 adenovirus vector, which expressed human interferon alfa-2b (IFNα-2b) cDNA under a cytomegalovirus promoter, was produced under good manufacturing practice conditions in 293 cells, as previously described, with slight modifications of the process. It was tested to be free of endotoxin, microbiologie contaminants, and other impurities. The structure of the vector was verified by sequencing. Production of recombinant IFNα-2b was verified from each production lot with immunologic methods. The excipient Syn3 is a polyamide surfactant that enhances adenoviral gene transfer to the bladder epithelium. Dose-dependent adenoviral gene transfer and urine concentrations of IFNα-2b were confirmed. Of 14 patients treated with dose levels of rAd-IFNα/Syn3 that resulted in measurable urine IFNα, six (43%) were free from recurrence at 3 months and had no dose-limiting toxicity, and two patients remained disease free at 29 and 39 months. 63 These provocative findings, predominantly at the two highest doses, prompted us to pursue a phase II study, designed to evaluate the efficacy and safety of intravesical rAd-65 IFNα/Syn3™ for patients with HG NMIBC refractory to, or with relapse after, BCG. This randomized, open-label, parallel-arm study was conducted across 13 centers in the United States between Nov. 5, 2012, and Apr. 8, 2015. The protocol, administrative oversight, and accrual timelines were designed and conducted by the Society of Urologic Oncology Clinical Trials Consortium. The study protocol and informed consent form were reviewed and approved by the respective responsible site institutional review boards and biosafety committees.

We assessed the efficacy and safety of recombinant adenovirus interferon alfa with Syn3™ (rAd-IFNα/Syn3™), a replication-deficient recombinant adenovirus gene transfer vector, for patients with high-grade (HG) BCG-refractory or relapsed NMIBC. In this open-label, multicenter (13 centers), parallel-arm, phase II study, of 43 patients with HG BCG-refractory or relapsed NMIBC received intravesical rAd-IFNα/Syn3™ (randomly assigned 1:1 to 1×1011 viral particles (vp)/mL or 3×1011 vp/mL). Patients who responded at months 3, 6, and 9 were retreated at months 4, 7, and 10. The primary end point was 12-month HG 78 recurrence-free survival (RFS). All patients who received at least one dose were included in 79 efficacy and safety analyses.

In our study, forty patients received rAd-IFNα/Syn3™ (1×1011 vp/mL, n=21; 3×1011 vp/mL., n=19) between Nov. 5, 2012, and Apr. 8, 2015. The trial was designed to enroll 40 patients unable or unwilling to undergo radical cystectomy, and there were two dosage groups of 20 patients each. Eligible patients were 18 years or older and had HG BCG-refractory or relapsed NMIBC, including papillary NMIBC alone (Ta or Tl), carcinoma in situ (CIS) alone, or a combination of CIS and papillary disease. BCG-refractory disease was defined as the inability to achieve a disease-free state at 6 months after adequate induction BCG therapy with either maintenance or reinduction at 3 months. "Adequate induction" was defined as a minimum of five of six treatments, and "adequate maintenance" was defined as a minimum of two of three treatments. BCG relapse was defined as recurrence within 1 year after a complete response to adequate BCG treatment (at least five and two instillations). Patients were required to have undergone visually complete resection of papillary lesions by transurethral resection of bladder tumors. Patients could not have received intravesical therapy within 3 months before beginning study treatment, with the exception of cytotoxic agents when administered as a single instillation immediately after a transurethral resection. All participants who entered the study provided written or oral informed consent.

Patients were assigned by computer-generated random assignment, with a constrained 1.1 sequence, to receive either low-dose ($1 \times 10^{11}$ viral particles [vp]/mL) or high-dose ($3 \times 10^{11}$ vp/mL) rAd-IFNα/Syn3. These doses were the most promising observed in the phase I study. The total doses administered were $7.5 \times 10^{12}$ vp in the low-dose group and 2.25/1013 vp in the high-dose group. Treatment allocation was performed centrally with a block size of two for all patients who had successfully completed screening, with the constraint that the first four patients at each site were balanced between cohorts.

rAd-IFNα/Syn3™ in 75 mL was administered intravesically through a urethral catheter, with a planned retention time of 1 hour, an anticholinergic treatment was allowed to relieve urinary urgency and permit adequate retention. Patients without recurrence of HG disease at months 3, 6, and 9, as evaluated by cytology, cystoscopy, and biopsy (if clinically indicated) were then retreated at months 4, 7, and 10. At 12 months, a final efficacy evaluation was performed. This evaluation included a protocol-mandated biopsy from the site of the index tumor and at least five random biopsies, including the bladder dome, trigone, right and left lateral wall, posterior wall, and prostatic urethra in men with positive cytology or prior disease in this region.

During the study, patients were contacted weekly by phone for the first month after each treatment on days 7, 14 (of months 7 and 10 only), 21, and 28 (+1 day) to provide information about adverse events (AEs) and concomitant medication use. Assessments for treatment failure were made between 14 and 7 days before retreatment. Patients who were withdrawn from treatment before study completion underwent a safety assessment at least 30 days after last administration of the study drug. All patients are being monitored in a 3-year long-term follow-up period to (1) determine recurrence of HG disease in those patients with a complete response and (2) to assess the long-term impact of treatment with rAd-IFNα/Syn3™.

The primary end point was freedom from HG disease recurrence at 12 months, defined by a negative for cause or end of study biopsy. Secondary end points included response to treatment, defined as no evidence of recurrence of HG disease at 3, 6, and 9 months; incidence and time to cystectomy, and concentration of IFNα-2b in the urine. Safety assessments included physical examination, monitoring of vital signs, ECG, and standard clinical chemistry, hematology, and urinalysis assessments (performed by local laboratories). Safety end points include type, incidence, relatedness, and severity of AEs and severe (2 grade 3) AEs (SAEs), as assessed by National Cancer Institute Common Terminology Criteria for Adverse Events (version 4.03).

We determined that a cohort of 20 patients would be sufficient to give an 80% probability of rejection of a HG recurrence-free survival (RFS) rate of 10% with an exact 5% one-sided test when the true HG RFS rate was 35%. The operating characteristics for this Fleming design were calculated exactly with the binomial distribution described by A'Hern. The hypothesis—that the response rate was equal to or less than the reference rate—was rejected if five or more of the 20 patients achieved HG RFS at 12 months. The proportion of patients who achieved HG RFS at 3, 6, 9, and 12 months was reported for each dose group, together with an exact 90% CI for the proportion. The time to HG recurrence or death was summarized with the Kaplan-Meier method. Analyses were performed with SAS™ (version 9 or later; SAS Institute, Cary, NC). Both the safety and efficacy (modified intention-to-treat) analysis sets included all patients who received at least one dose of rAd-IFNα/Syn3. A data monitoring committee oversaw the study according to the data monitoring plan. All analytical assays were developed and validated Samples were tested according to good laboratory practices methods at Covance Laboratories Ltd (Harrogate, United Kingdom).

Baseline patient characteristics are provided in Table 1:

TABLE 1

Baseline Patient Characteristics

| Characteristics | No. (%) by rAd-IFNα/Syn3 Dose Group | | No. (%) |
| --- | --- | --- | --- |
| | $1 \times 10^{11}$ vp/mL (n = 21) | $3 \times 10^{11}$ vp/mL (n = 19) | Overall (N = 40) |
| Median (IQR) age, years | 70 (67-74) | 73 (62-81) | 70.5 (64.5-77.5) |
| Sex | | | |
| Male | 19 (90) | 14 (73.7) | 33 (82.5) |
| Female | 2 (9.5) | 5 (26.3) | 7 (17.5) |
| ECOG PS | | | |
| 0 | 16 (76.2) | 18 (94.7) | 34 (85.0) |
| 1 | 5 (23.8) | 1 (5.3) | 6 (15.0) |
| History of radiation therapy* | 1 (4.8) | 1 (5.3) | 2 (5) |
| BCG failure classification | | | |
| Relapsed | 10 (47.6) | 9 (47.4) | 19 (47.5) |
| Refractory | 11 (52.4) | 10 (52.6) | 21 (52.5) |
| No. of previous BCG courses | | | |
| 1 | 1 | 1 | 2 |
| 2 | 10 | 12 | 22 |
| >3† | 10 | 6 | 16 |
| Primary tumor classification at enrollment | | | |
| CIS | 12 (57.1) | 9 (47.4) | 21 (52.5) |
| Ta | 2 (9.5) | 2 (10.5) | 4 (10) |

TABLE 1-continued

Baseline Patient Characteristics

| Characteristics | No. (%) by rAd-IFNα/Syn3 Dose Group | | No. (%) Overall (N = 40) |
|---|---|---|---|
| | 1 × 10$^{11}$ vp/mL (n = 21) | 3 × 10$^{11}$ vp/mL (n = 19) | |
| Ta and CIS | 3 (14.3) | 1 (5.3) | 4 (10) |
| T1 | 2 (9.5) | 4 (21.1) | 6 (15) |
| T1 and CIS | 2 (9.5) | 3 (15.8) | 5 (12.5) |

Abbreviations: BCG, *bacillus* Calmette-Guerin; CIS, carcinoma in situ; ECOP PS, Eastern Cooperative Oncology Group performance status; IQR, interquartile range; rAd-IFNα/Syn3, recombinant adenovirus interferon alpha protein/Syn3 (a nonreplicating recombinant adenovirus gene transfer vector for patients with high-grade BCG-refractory or relapsed non-muscle-invasive bladder cancer); Ta, papillary urothelial carcinoma confined to the mucosa; T1, micro-invasive urothelial carcinoma invasive into lamina propria but not muscularis propria; vp, viral particles.
*Radiology was 10 or more years before screening in each of these three patients; as such, they were deemed eligible for study enrollment.
†Range of previous courses, 3 to 8.

The 12-month HG RFS rate was comparable between the two dose groups, with 33.3% of patients (7 of 21: 90% CI, 16.8 to 53.6) in the low-dose group and 36.8% (7 of 19; CI, 18.8 to $8.2) in the high-dose group alive and free of HG disease at 12 months. Overall, 35.0% of patients (14 of 40; 90% CI, 22.6% to 49.2%) remained free of HG recurrence at 12 months after the initiation of rAd-IFNα/Syn3 treatment. Off-schedule disease assessments did not affect findings (Appendix, online only). The median time to HG recurrence or death was 6.5 months (90% CI, 3.52 to 12.78 months); the median time to HG recurrence was 3.52 months (90% CI, 3.02 to 12.78 months) for the low-dose group and was 11.73 months (90% CI, 5.88 months to not evaluable) for the high-dose group.

Fourteen patients (35.0%; 90% CI, 22.6% to 49.2%) remained free of HG recurrence 12 months after initial treatment. Comparable 12-month HG RFS was noted for both doses. Of these 14 patients, two experienced recurrence at 21 and 28 months, respectively, after treatment initiation, and one died as a result of an upper tract tumor at 17 months without a recurrence. rAd-IFNα/Syn3 was well tolerated; no grade four or five adverse events (AEs) occurred, and no patient discontinued treatment because of an adverse event. The most frequently reported drug-related AEs were micturition urgency (n=16; 40%), dysuria (n=16; 40%), fatigue (n=13; 32.5%), pollakiuria (n=11; 28%), and hematuria and nocturia (n=10 each; 25%).

When patient subgroups and secondary end points were considered in exploratory analyses, the 12-month HG RFS rates were broadly similar for men and women, for younger and older patients, for refractory or relapsed NMIBC, for CIS only or papillary tumors and CIS, and for patients with Ta and TI disease only.

TABLE 2

Incidence of HG RFS at 3, 6, 9 and 12 Months

| | rAd-IFNα/Syn3 Dose Group | | | | | |
|---|---|---|---|---|---|---|
| | 1 × 10$^{11}$ vp/mL (n = 21) | | 3 × 10$^{11}$ vp/mL (n = 19) | | Overall (N = 40) | |
| Variable | No. (%) of Patients | 90% Cl (%)* | No. (%) of Patients | 90% Cl (%)* | No. (%) of Patients | 90% Cl (%)* |
| RFS at secondary end point analysis time | | | | | | |
| 3 months | 10 (47.6) | 28.6 to 67.2 | 13 (68.4) | 47.0 to 85.3 | 23 (57.5) | 43.3 to 70.8 |
| 6 months | 8 (38.1) | 20.6 to 58.3 | 9 (47.4) | 27.4 to 68.0 | 17 (42.5) | 29.2 to 56.7 |
| 9 months | 8 (38.1) | 20.6 to 58.3 | 9 (47.4) | 27.4 to 68.0 | 17 (42.5) | 29.2 to 56.7 |
| 12 months | 7 (33.3) | 16.8 to 53.8 | 7 (36.8) | 18.8 to 58.2 | 14 (35.0) | 22.6 to 49.2 |
| HG recurrence-free subgroup at 12 months | | | | | | |
| Refractory NMIBC (n = 31) | | | | | 8 (38.1) | 20.6 to 58.3 |
| Relapsed NMIBC (n = 19) | | | | | 6 (31.6) | 14.7 to 53.0 |
| CIS only (n = 21) | | | | | 6 (28.6) | 13.2 to 48.7 |
| Papillary tumor (n = 9) | | | | | 3 (33.3) | 9.7 to 65.6 |
| Ta + T1 disease only (n = 10) | | | | | 5 (50.0) | 22.2 to 77.8 |
| Serum antiadenoviral antibody | | | | | | |
| Positive (n = 22) | | | | | 10 (45.5) | 27.1 to 64.7 |
| Negative (n = 17) | | | | | 4 (23.5) | 8.5 to 46.1 |

Abbreviations: CIS, carcinoma in situ; GG, high-grade; NMIBC, non-muscle-invasive bladder cancer; rAd-IFNα/Syn3, recombinant adenovirus interferon alpha protein/Syn3 (a nonreplicating recombinant adenovirus gene transfer vector for patients with high-grade bacillus Calmette-Guerin-refractory or relapsed NMIBC); RFS, relapse-free survival; Ta; papillary urothelial carcinoma confined to the mucosa; T1; micro invasive urothelial carcinoma invasive into lamina propria but not muscularis propria; vp, viral particles.
*CI is for the proportion of patients with HG RFS; 90% CIs are based on the exact binomial method.

Interestingly, of the 14 patients who were recurrence free at 12 months, 10 (71%) of the 14 had an antiadenovirus antibody response (defined as four times the predose titer), compared with (24%) of 25 who experienced recurrence.

In long-term follow-up, seven patients (18%) who withdrew from the study because of HG disease recurrence within the 12-month study period died at a median of 16 months (range, 2 to 26 months) after the withdrawal date. There is no indication that these deaths were treatment related. The cause of death was unknown in four patients, whereas two died as a result of progressive bladder cancer and one died as a result of liver failure unrelated to treatment 17 months after withdrawal from the study. The four patients for whom the cause of death is unknown were being observed locally after they completed their end-of-study evaluation. Fourteen patients (35%) who experienced an HG recurrence within the first year underwent a radical cystectomy at a median of 9 months (range, 4 to 28 months) from day 1 of month 1.

Patients are being monitored for 3 years to collect long-term follow-up data. Of the 14 patients who remained disease free at 12 months, additional follow-up data are being collected for 11; 3 withdrew from the study. Nine of these 11 patients are alive, and eight remained disease-free during a period of 15 to more than 36 months. Two patients experienced HG recurrence at 21 and 28 months, respectively, from the start of treatment. One of these patients who experienced progression to muscle invasion underwent a radical cystectomy 31 months after the initiation of treatment and later died at 41 months. The other, who experienced recurrence at 21 months, remained alive and free from distant recurrence at 36 months. One patient free from bladder recurrence at 12 months died as a result of an upper tract tumor at 17 months.

TABLE 3

Durability of HG RFS Since Start of Treatment With rAd-IFNα/Syn3

| Stage at Entry | Dose Group | Duration of Bladder HG RFS Since Day 1 (months) | Time of Last Follow-Up from Day1 (months) | Status at Last Follow-Up |
|---|---|---|---|---|
| Ta/CIS | High | 21 | 47 | Recurrence of HGD Died at 38 months |
| Ta | Low | 28 | 41 | Recurrence of 28 months Cystectomy at 31 months Died at 41 months |
| CIS | Low | 15 | 15 | CR Withdrew |
| Ta/CIS | Low | 30 | 36 | Recurrence of HGD |
| Ta | High | 16 | 16 | CR Withdrew |
| T1/CIS | Low | 35 | 37 | CR |
| T1 | Low | 30 | 50 | CR |
| T1 | High | 36 | 36 | CR |
| CIS | High | 38 | 39 | CR |
| CIS | High | 34 | 37 | CR |
| CIS | High | 27 | 27 | CR |
| CIS | Low | 34 | 37 | CR |
| T1/CIS | Low | 17 | 17 | Died of upper tract recurrence |
| Ta | High | 13 | 13 | CR Withdrew |

NOTE.
Duration of HG RFS represent the number of months from day 1 that a complete response within the bladder has been documented based on yearly report. Three patients withdrew from the study after the 1-month end-of-study evaluation. Two patients had recurrence of HGD at 21 and 28 months from day 1. One of these patients underwent a cystectomy but later died. One patient died of an upper tract tumor with a bladder recurrence.
Abbreviations: CIS, carcinoma in situ; CR, complete response; HG, high-grade; HGD, high-grade disease; rAd-IFNα/Syn3, recombinant adenovirus interferon alpha protein/Syn3 (a nonreplicating recombinant adenovirus gene transfer vector for patients with HG bacillus Calmette-Guerin-refractory or relapsed non-muscle-invasive-bladder cancer); RFS, relapse-free survival; Ta, papillary urothelial carcinoma confined to the mucosa; T1, micro-invasive urothelial carcinoma invasive into lamina propria but not muscularis propria.

Our results showed that rAd-IFNα/Syn3™ was well tolerated. It demonstrated promising efficacy for patients with HG NMIBC after BCG therapy who were unable or unwilling to undergo radical cystectomy.

While potentially promising, however, these data show several failings in our treatment plan. First, treatment was ineffective in the majority of patients: fully 65% of patients failed to achieve a 12-month HG RFS by intention-to-treat analysis of all patients dosed. Likewise, the 12-month RFS in heavily pretreated patients was 31%. Notably, responses were durable: the majority remained disease-free for close to 24 months. We noted that for patients with any element of CIS, 70% failed to achieve a durable complete response. Indeed, for patients with papillary disease only at study entry, only 50% achieved RFS.

To address these failings, we have pursued two approaches. First, we have designed and are currently pursuing a larger trial involving significantly more patients and a high-dose of rAd-IFNα/Syn3™. This trial may provide evidence that a higher dose of rAd-IFNα/Syn3™ is effective where a lower dose was not merely less effective, but entirely ineffective.

Second, we collected tissue samples from patients involved in the above-discussed Phase II completed trial. These samples enable us to analyze gene expression for each patient. This enables us to compare gene expression in patients who responded to treatment against gene expression in patients who did not respond.

Gene expression analysis may be done using tumor biopsy samples.

Alternatively, for bladder cancer, urine samples if properly preserved may contain exosomes which enable analysis of oncogene expression. Exosomes are small (30-100 nm) endocytic, cell-derived vesicles. They are secreted by most human cell types, including cancer cells, and they may be absorbed via endocytosis into recipient cells. Exosomes can contain functional bio-molecules such as dsdna, and may be found in human blood and urine. Exosomal DNA ("exoDNA") represents the entire genome and, where the exosome is produced from a tumor cell, reflects the mutational status of the tumor cell. ExoDNA in tumor-derived exosomes found in a urine sample taken from a bladder cancer patient thus provides a non-invasive circulating biomarker useful for the sensitive detection of cancer and a more accurate determination of potential responsiveness to interferon-based therapies.

ExoDNA includes both single-stranded and double-stranded DNA. ExoDNA is found encapsulated in the interior of the exosome membrane and bound to the exterior of the exosome membrane. In internal exoDNA, dsDNA predominates. Typically, exoDNA encapsulated in the interior of the exosome membrane ranges from 0.1-2.5 kb, while exoDNA bound to the exosome membrane exterior is >2.5 kb. Much of the exoDNA associated with tumor exosomes is double-stranded DNA bound to the exterior of the exosome membrane. ExoDNA, which includes dsDNA, can provide an unusually accurate diagnostic tool because it provides a complete sample of the complete genome in readily-assayable form in the urine of a patient with bladder cancer.

Alternatively, one can assay micro vesicles. Micro vesicles are another type of extracellular vesicle, between 50 and 1,000 nanometers (nm) in diameter, found in many types of body fluids as well as the interstitial space between cells. Micro vesicles are made from fragments of plasma membrane. They are thus distinct from exosomes, which are smaller and generated intra-cellularly. In contrast to exosomes, which do not contain mitochondrial DNA, micro vesicles derived from astrocytes and glioblastoma include mitochondrial DNA. Micro vesicles appear equivalent to exosomes for the purposes of this invention.

For a human patient diagnosed with bladder cancer, one may collect exosomes by collecting a urine sample. Sample storage techniques able to preserve DNA and RNA are known in the art. Similarly, isolation of exosomes from urine may be done using conventional separation techniques.

Alternatively, one may employ fluorescent in situ hybridization (FISH). FISH is a molecular cytogenetic technique that uses fluorescent probes that bind to specific target parts of the chromosome, but when adequately stringent hybridization conditions are used, does so with a high degree of sequence complementarity. FISH was developed in the early 1980s. See e.g., Langer-Safer, P. R. et al., Imnunological Method For Mapping Genes On *Drosophila* Polytene Chromosomes, 79 Proceedings of the National Academy of Sciences 4381 (1982). FISH can detect and localize the presence or absence of specific DNA sequences on chromosomes or in DNA fragments such as free DNA found in urine.

To use FISH in our diagnostic method, one constructs a probe able to hybridize with a portion of CDKN2A, and preferably with one or more of the eight exons contained in CDKN2A. The probe must be large enough to hybridize specifically with its target but not so large as to require non-stringent hybridization conditions, which conditions may lead to formation of false-positive hybridization to an inappropriate target sequence. We prefer a probe of about 40 bp, but longer or shorter may be used depending on the specific CDKN2A mutation sought. Once made, the probe is tagged directly with fluorophores, with targets for antibodies or with biotin. Tagging can be done in various ways taught in the art, such as nick translation or Polymerase Chain Reaction using tagged nucleotides.

To find out whether and where the fluorescent probe is bound to the target DNA in e.g., a urine sample, one may use fluorescence microscopy. FISH can also be used to detect and localize specific RNA targets (e.g., mRNA) in cells, circulating tumor cells, and tissue samples.

As an alternative to sequencing exoDNA in a urine sample, one may isolate free DNA from the urine sample and sequence that free DNA.

Analysis of exoDNA reveals a critical difference in the populations of bladder cancer patients who respond to interferon therapy and those who do not. Patients who respond to treatment have a different level of expression of CDKN2A than do patients who do not respond to treatment. These different levels in expression appear to arise from deletions in the gene, or a loss of heterozygosity in the gene.

Our insight can improve the safety and efficacy of rAd-IFN gene therapy because it enables the attending physician to limit treatment to those patients most likely to respond. Further, our insight can similarly improve the safety and efficacy of other instilled treatments which induce interferon expression, e.g., BCG vaccine. Similarly, our insight can improve the effectiveness of cancer "checkpoint inhibitors." Checkpoint inhibitors are thought to be ineffective in cancer patients with CDKN2A deletions. Identifying such patients enables the artisan to combine interferon therapy with checkpoint inhibitor therapy in such patients, using the interferon to overcome the inhibition of the checkpoint inhibitor.

We thus here intend this patent to cover a method of treating bladder cancer, comprising diagnosing bladder cancer in a human, measuring the human's level of CDKN2A expression, and then instilling into the human an agent which induces interferon expression.

We similarly intend this patent to cover that method of treating bladder cancer, where the bladder cancer is high-grade.

We similarly intend this patent to cover that method of treating bladder cancer, where the agent is a non-replicating agent such as rAd-IFN or *mycobacterium* cell wall extract.

We similarly intend this patent to cover that method of treating bladder cancer, where the agent is a replicating agent such as BCG vaccine.

We similarly intend this patent to cover that method of treating bladder cancer, where measuring the human's level of CDKN2A expression entails taking a bladder tissue sample and measuring the level of CDKN2A expression in that tissue sample. Alternatively, we intend this patent to cover that method of treating bladder cancer, where measuring the human's level of CDKN2A expression entails taking a urine sample, and measuring the level of CDKN2A expression in it, preferably by analyzing the exosomes in it, but also by analyzing e.g., free DNA in it.

We similarly intend this patent to cover that method of treating bladder cancer, where the human also gets treated with a cancer checkpoint inhibitor.

We similarly intend our patent to cover a companion diagnostic test able to measure the level of CDKN2A expression in a bladder tissue sample.

Further embodiments and variations will be readily apparent to the artisan after reviewing this disclosure. We thus intend our appended legal claims to encompass such embodiments.

I claim:

1. A method of treating *Bacillus* Calmette-Guérin unresponsive non-muscle invasive bladder cancer in a human, comprising:
   a. diagnosing *Bacillus* Calmette-Guérin unresponsive non-muscle invasive bladder cancer in a human,
   b. measuring a level of CDKN2A expression in a sample obtained from the human,
   c. selecting a human based on the level of CDKN2A expression measured in step b), and
   d. instilling into the lumen of the bladder of said human selected from step c) with a non-replicating vector comprising nadofaragene firadenovec.

2. The method of claim 1, where the bladder cancer is high-grade.

3. The method of claim 1, where said measuring the human's level of CDKN2A expression entails taking a bladder tissue sample and measuring the level of CDKN2A expression in that tissue sample.

4. The method of claim 1, wherein said measuring the human's level of CDKN2A expression entails taking a urine sample and measuring the level of CDKN2A expression in it.

5. The method of claim 4, wherein said measuring the level of CDKN2A expression comprises analyzing the exosomes in said urine sample.

6. The method of claim 4, wherein said measuring the level of CDKN2A expression comprises analyzing fee DNA in said urine sample.

7. The method of claim 1, further comprising the step of administering to said human a checkpoint inhibitor after said step of measuring the level of CDKN2A expression.

8. The method of claim 1, wherein said step of measuring the human's level of CDKN2A expression comprises using fluorescent in situ hybridization using a probe able to hybridize with a portion of CDKN2A.

9. The method of claim 8, wherein said probe comprises a portion which hybridizes with at least one exon contained in CDKN2A.

10. The method of claim 8, wherein said probe is about 40 bp in length.

11. The method of claim 9, wherein said probe is about 40 bp in length.

12. A method of treating *Bacillus* Calmette-Guérin unresponsive non-muscle invasive bladder cancer in a human, comprising:
    a. diagnosing *Bacillus* Calmette-Guérin unresponsive non-muscle invasive bladder cancer in a human,
    b. measuring a level of CDKN2A expression in an urine sample obtained from the human, wherein measuring the level of CDKN2A expression comprises analyzing exosomes or free DNA in the urine sample,
    c. selecting a human based on the level of CDKN2A expression measured in step b), and
    d. instilling into the lumen of the bladder of said human selecting in step c) with a non-replicating vector comprising nadofaragene firadenovec.

13. The method of claim 12, wherein said step of measuring the human's level of CDKN2A expression comprises using fluorescent in situ hybridization using a probe able to hybridize with a portion of CDKN2A.

14. The method of claim 12, wherein said probe comprises a portion which hybridizes with at least one exon contained in CDKN2A.

15. The method of claim 13, wherein said probe is about 40 bp in length.

16. The method of claim 14 wherein said probe is about 40 bp in length.

* * * * *